(12) United States Patent
Puckette et al.

(10) Patent No.: US 7,420,093 B2
(45) Date of Patent: Sep. 2, 2008

(54) PROCESS FOR THE PREPARATION OF GLYCOLALDEHYDE

(75) Inventors: Thomas Allen Puckette, Longview, TX (US); Thomas James Devon, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/854,210

(22) Filed: Sep. 12, 2007

(65) Prior Publication Data

US 2008/0081931 A1 Apr. 3, 2008

Related U.S. Application Data

(60) Provisional application No. 60/827,486, filed on Sep. 29, 2006.

(51) Int. Cl.
C07C 45/50 (2006.01)

(52) U.S. Cl. ........................ 568/454; 568/458

(58) Field of Classification Search .............. 568/454, 568/458

See application file for complete search history.

(56) References Cited

U.S. PATENT DOCUMENTS

| | | |
|---|---|---|
| 3,560,539 A | 2/1971 | Booth |
| 3,920,753 A | 11/1975 | Yukawa et al. |
| 3,948,965 A | 4/1976 | Cawse |
| 4,072,720 A | 2/1978 | Haag et al. |
| 4,291,179 A | 9/1981 | Goetz et al. |
| 4,317,946 A | 3/1982 | Costa |
| 4,321,414 A | 3/1982 | Costa |
| 4,362,820 A | 12/1982 | Kaplan |
| 4,382,148 A | 5/1983 | Drent |
| 4,390,734 A | 6/1983 | Knifton |
| 4,405,814 A | 9/1983 | Carroll et al. |
| 4,405,821 A | 9/1983 | Goetz |
| 4,450,299 A | 5/1984 | Oswald et al. |
| 4,477,685 A | 10/1984 | Chan |
| 4,496,781 A | 1/1985 | Jacobson et al. |
| 4,503,260 A | 3/1985 | Auvil et al. |
| 4,533,756 A | 8/1985 | Lin et al. |
| 4,533,774 A | 8/1985 | Lin et al. |
| 4,560,806 A | 12/1985 | Jacobson |
| RE32,084 E | 2/1986 | Goetz |
| 4,590,298 A | 5/1986 | Che |
| 4,608,444 A | 8/1986 | Jacobson |
| 4,687,866 A | 8/1987 | Oswald et al. |
| 4,687,874 A | 8/1987 | Oswald et al. |
| 4,740,525 A | 4/1988 | Maerkl |
| 4,847,423 A | 7/1989 | Koprowski et al. |
| 5,059,710 A | 10/1991 | Abatjoglou et al. |
| 5,756,855 A | 5/1998 | Abatjoglou et al. |
| 5,840,647 A | 11/1998 | Puckette et al. |
| 6,130,358 A | 10/2000 | Tolleson et al. |
| 6,191,324 B1 | 2/2001 | Guram et al. |
| 6,515,161 B1 | 2/2003 | Kreutzer et al. |
| 6,525,161 B1 | 2/2003 | Hall |
| 6,677,268 B2 | 1/2004 | Hillebrand et al. |
| 6,693,219 B2 | 2/2004 | Puckette et al. |
| 6,831,035 B2 | 12/2004 | Puckette et al. |
| 6,846,960 B2 | 1/2005 | Tolleson et al. |
| 6,906,225 B2 | 6/2005 | Puckette et al. |
| 6,995,292 B2 | 2/2006 | Tolleson et al. |
| 2004/0059153 A1 | 3/2004 | Magna et al. |
| 2004/0152928 A1 | 8/2004 | Drent et al. |

FOREIGN PATENT DOCUMENTS

| | | |
|---|---|---|
| EP | 002908 | 7/1979 |
| EP | 0331512 | 9/1989 |
| GB | 1585604 | 3/1981 |
| JP | 57118527 | 7/1982 |
| JP | 62209032 | 9/1987 |
| SU | 1310383 | 5/1987 |
| WO | WO 2005058788 | 6/2005 |
| WO | WO 2005063668 | 7/2005 |

OTHER PUBLICATIONS

Co-pending U.S. Appl. No. 11/670,628, filed Feb. 2, 2007.
Baricelli et al, "*Homogeneous Catalysis Reaction of Formaldehyde with Synthesis Gas Using Rhodium Complexes*" http://www.scielo.cl/scielo.php?script=sci_arttext&pid=S036616442000000300008&lng=en&nrm=iso&tlng=en (believed to have been downloaded Jul. 14, 2006).
Chan et al, "*Rhodium-Catalyzed Hydroformylation of Formaldehyde*", Journal of Molecular Catalysis, 19, (1983) pp. 377-391.
Jacobson, "*Formaldehyde Hydroformylation to Glycol Aldehyde Via Rhodium Phosphine-Amine and Phosphine-Amide Catalysts*", Journal of Molecular Catalysis, 41 (1987) pp. 163-183.
Marchionna et al, "*Hydroformylation of Formaldehyde Catalyzed by $Rh_4(CO)_{12}$ In the Presence of Phosphine Ligands and Acids (*)*", Gazzetta Chimica Italiana, 116 (1986) pp. 453-457.
Marchionna, M. "Oxygenates by Homologation of CO Hydrogenation With Metal Complexes" in *Catalysis By Metal Complexes*, vol. 16 (1994), Edited by G. Braca; Kluwer Academic Publishers (Dordrecht), pp. 191-219.
Notice of Allowance dated Jul. 16, 2007 for Copending U.S. Appl. No. 11/693,542, filed Mar. 29, 2007.

*Primary Examiner*—Sikarl A Witherspoon
(74) *Attorney, Agent, or Firm*—Eric D. Middlemas; Bernard J. Graves, Jr.

(57) ABSTRACT

Disclosed are processes for the preparation of glycolaldehyde in which formaldehyde is contacted with carbon monoxide and hydrogen in the presence of a rhodium catalyst and a solvent containing at least one N,N-dihexylbutyramide. The glycolaldehyde product is recovered by extraction with water. The process provides high selectivity to glycolaldehyde and efficient separation of hydroformylation products from the solvent and rhodium catalyst.

20 Claims, No Drawings

PROCESS FOR THE PREPARATION OF GLYCOLALDEHYDE

CROSS REFERENCES TO RELATED APPLICATIONS

This application claims the benefit of U.S. Provisional Application Ser. No. 60/827,486, filed Sep. 29, 2006, which is incorporated herein by reference in its entirety.

FIELD OF THE INVENTION

This invention pertains processes for the hydroformylation of formaldehyde to glycolaldehyde. More specifically, this invention pertains to hydroformylation processes in which formaldehyde is contacted with carbon monoxide, hydrogen, rhodium and a hydroformylation solvent comprising at least one N,N-dihexylbutyramide and in which the glycolaldehyde product is recovered by extraction with water.

BACKGROUND OF THE INVENTION

Glycolaldehyde is an intermediate in many organic reactions and is particularly useful as an intermediate in the production of ethylene glycol through a catalytic hydrogenation process. Ethylene glycol is a valuable commercial chemical with a wide variety of uses, e.g., as a coolant and antifreeze, monomer for polyester production, solvent, and an intermediate for production of commercial chemicals.

Glycolaldehyde can be prepared by the rhodium catalyzed hydroformylation of formaldehyde under elevated temperatures and pressures. The hydroformylation reaction is typically carried out in an aprotic solvent which will dissolve polar materials. Suitable solvents include a wide variety and are exemplified by N,N-disubstituted amides, in which each hydrogen of the amido nitrogen is substituted by a hydrocarbon group, e.g., 1-methylpyrrolidin-2-one, N,N-dimethylacetamide, N,N-diethylacetamide, and N,N-dimethylformamide; nitriles, such as acetonitrile, benzonitrile, propionitrile and the like; cyclic ethers such as tetrahydrofuran, dioxane and tetrahydropyran; ethers such as diethyl ether, 1,2-dimethoxybenzene, alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; and esters, such as ethyl acetate, ethyl propionate and methyl laurate.

The separation of the glycolaldehyde product from the hydro-formylation reaction mixture in these processes, however, is often difficult and expensive because of the thermal sensitivity of the catalyst and reactivity of the the glycolaldehyde product. For example, the separation of glycolaldehyde from the hydroformylation catalyst solution by traditional distillation methods can be difficult because of the decomposition hydroformylation catalyst and the formation of glycolaldehyde byproducts. Various techniques for accomplishing this separation have been disclosed and include, for example, distillation (British Patent No.1,585,6004 and U.S. Pat. No.'s Re. 32,084 and 4,405,851), separation of glycolaldehyde as a distinct polar phase from the non-polar catalyst components (U.S. Pat. No.'s 4,496,781, 4,560,806, and 4,608,444), and extraction (U.S. Pat. No.'s 4,503,260; 4,405,814; 4,740,525; 4,477,685 and 4,382,148). These methods, however, are subject to various shortcomings. For example, distillation of the reaction mixture subjects the catalyst to conditions which can result in the decomposition of ligands and/or the irreversible precipitation of rhodium metal. Distillation, in some instances, can result in the formation of metallic mirrors on the surface of process equipment. In addition, distillation can greatly reduce the activity of the catalyst. The conversion of the glycolaldehyde product to an acetal or hemiacetal may improve its thermal sensitivity, but does not solve the problem of catalyst decomposition. This approach also suffers from the disadvantage that an additional hydrolysis step is required to obtain the glycolaldehyde product.

Glycolaldehyde may also be separated using extraction techniques. It can be difficult, however, to separate the glycolaldehyde into an easily isolated form without the simultaneous extraction of significant amounts of expensive rhodium catalyst or reaction solvent. Residual catalyst and solvent can interfere with the conversion of glycolaldehyde into further products such as ethylene glycol. In addition, it is sometimes necessary to recycle the organic phase from the extraction to reuse the solvent and catalyst in subsequent reactions. With extraction, it is also difficult to balance catalyst activity, glycolaldehyde extractability, and rhodium retention in the organic phase.

For example, lower molecular weight amide solvents such as, for example, dimethylformamide, dimethylacetamide, N,N-dimethylbutyramide, and N-methylpyrollidinone (NMP), give good catalyst activity, but are readily extracted into the aqueous phase along with some of the rhodium catalyst. Higher molecular weight amides, by contrast, can give better extraction performance but typically exhibit poor reaction rates. In view of the problems that remain in the art, there is a need for a process for the hydroformylation of formaldehyde to glycolaldehyde that can provide good reaction rates and selectivity to glycolaldehyde, allows for clean separation of the product and catalyst, and enables efficient recovery and recycle of the catalyst and solvent.

BRIEF SUMMARY OF THE INVENTION

We have found that the hydroformylation of formaldehyde to glycolaldehyde can be carried in the presence of certain amide solvents that, in some embodiments, provide good conversion and high selectivity to glycolaldehyde and enables the separation of the glycolaldehyde product from the reaction mixture by a simple aqueous extraction step. One embodiment of the instant invention, therefore, is a process for the preparation of glycolaldehyde, comprising: (i) contacting hydrogen, carbon monoxide, and formaldehyde in the presence of a catalyst comprising rhodium and a solvent comprising at least one N,N-dihexylbutyramide to form a reaction mixture comprising glycolaldehyde; and (ii) contacting the reaction mixture with water to produce an organic layer comprising the rhodium catalyst and the hydroformylation solvent, and an aqueous layer comprising the glycolaldehyde. Although not a critical aspect of the invention, the extraction step in our process can transfer 85 weight percent or greater of the glycolaldehyde present in the reaction mixture to the aqueous extract after a single extraction. In another, embodiment of the invention, this aqueous extract can be substantially free of the organic amide solvent and the rhodium catalyst. For example, the rhodium content of the aqueous extract can be less than 1 ppm. In other embodiments, our process can operate under moderate temperatures and pressures. The rhodium catalysts of the invention may further comprise at least one trivalent organophosphorus ligand such as, for example, at least one tertiary phosphine, tertiary phosphite, fluorophosphite, or combinations thereof.

Another embodiment of our invention is a process for the preparation of glycolaldehyde, comprising: (i) contacting hydrogen, carbon monoxide, and formaldehyde in the presence of a catalyst comprising rhodium and an organic ligand comprising one or more tertiary phosphines, tertiary phosphites, fluorophosphites, or combinations thereof; and a solvent comprising N,N-di-n-hexyl-n-butyramide, N,N-di-n-hexyl-isobutyramide, or a mixture thereof, at a temperature of about 75 to about 135° C. and a pressure of about 105 to about 175 bar absolute, to form a reaction mixture comprising glycolaldehyde; (ii) contacting the reaction mixture with water to produce an organic layer comprising the rhodium catalyst and the hydroformylation solvent, and an aqueous layer comprising the glycolaldehyde; (iii) separating the organic and aqueous layers; and (iv) recycling the organic layer to step (i).

DETAILED DESCRIPTION

The present invention provides a process for the preparation of glycolaldehyde comprising (i) contacting hydrogen, carbon monoxide, and formaldehyde in the presence of a catalyst comprising rhodium and a solvent comprising at least one N,N-dihexylbutyramide to form a reaction mixture comprising glycolaldehyde; and (ii) contacting reaction mixture with water to produce an organic layer comprising the rhodium catalyst and the hydroformylation solvent, and an aqueous layer comprising the glycolaldehyde. In one embodiment of the invention, the aqueous layer can contain a major portion of the glycolaldehyde product produced in the reaction and can be substantially free of the amide solvent and rhodium catalyst. In another embodiment, the organic layer containing the catalyst and the amide solvent can be recycled to the process with little or no purification.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, references to a "ligand," or a "reactor" is intended to include the one or more ligands or reactors. References to a composition or process containing or including "an" ingredient or "a" step is intended to include other ingredients or other steps, respectively, in addition to the one named.

The terms "containing" or "including", are synonymous with the term "comprising", and is intended to mean that at least the named compound, element, particle, or method step, etc., is present in the composition, article, or method, but does not exclude the presence of other compounds, catalysts, materials, particles, method steps, etc, even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The term "substantially free", as used herein in context with the amide and rhodium content of the aqueous extract, is understood to mean that the aqueous extract typically contains 1 part-per-million (ppm) or less by weight rhodium and 0.5 weight percent or less of the amide after extraction of the hydroformylation reaction mixture with approximately an equal volume of water. The term "N,N-dihexylbutyramide", as used herein, is understood to mean an amide of n-butyric or isobutyric acid in which each amido hydrogen is substituted with a linear or branched, hydrocarbyl group containing 6 carbon atoms. The term "N,N-dihexylbutyramide" is intended include all isomers of N,N-dihexylbutyramides, individually or as mixtures of isomers. Some examples of such isomers include, but are not limited to, N,N-di-n-hexyl-n-butyramide, N,N-diisohexyl-n-butyramide, N,N-di-n-hexyl-isobutyramide, N,N-diisohexyl-isobutyramide, and N-hexyl, and N-isohexyl-n-butyramide. The term "fluorophosphite", as used herein, is understood to mean a trivalent, organophosphorus compound having the general formula $(RO)_2P$—F, in which R represents the same or different organic groups. The term "ligand", as used herein, is intended to have its commonly accepted meaning as would be understood by persons having ordinary skill in the art, that is a molecule, atom, ion, or group of atoms that is bound or capable of binding to a central atom as a chelate or coordination compound. In the present invention, trivalent organophosphorus compounds can serve as ligands bound to a central rhodium atom. The prefix "organo", as used herein, is intended to have its commonly accepted meaning of "carbon-containing". Thus, an organophosphorus compound is a compound containing carbon and phosphorus. The term "trivalent", as used herein, is understood to mean "having a chemical valence or bonding capability of three". Thus, the term trivalent phosphorus compound is intended to mean a phosphorus compound bonded to three substituents and having a free pair of electrons. The term "tertiary", as used herein, is understood also to have its commonly accepted meaning in the chemical arts of an atom substituted with three radicals or substituents. For example, a tertiary phosphine is a phosphine in which the phosphorus atom bears three organic groups or substituents. Similarly, a tertiary phosphite is synonymous with the term "tertiary phosphite ester", and means a triester of phosphorous acid having the general formula $P(OR)_3$, in which R represents the same or different organic groups. The term "hydroformylation", as used herein, also is understood to have its commonly accepted meaning of a catalytic process in which hydrogen and carbon monoxide are reacted with a double bond resulting in the net addition of a formyl group and hydrogen across that double bond. The double bond typically is a carbon-carbon double bond but, as in the case of the present invention, also can be the carbon-oxygen double bound of formaldehyde. The term "formaldehyde", as used herein, is intended to include monomeric formaldehyde and any formaldehyde source that is readily converted to formaldehyde under the conditions of the hydroformylation reaction. For example, "formaldehyde", as used herein, would include formaldehyde in its monomeric form as well as its various acetals, hemiacetals, and low molecular weight oligomers such as, for example, paraformaldehyde. Similarly, the term "glycolaldehyde", is intended to include 2-hydroxyacetaldehyde and any derivatives thereof such as, for example, acetals, ethers, hemiacetals, oligomers, and hydrogenated products, that may be produced from glycolaldehyde under hydroformylation reaction conditions.

The hydrogen:carbon monoxide mole ratio used in the process of the invention may vary considerably and range from about 10:1 to about 1:10. The sum of the absolute partial pressures of hydrogen and carbon monoxide may range from 0.5 to 350 bars absolute. The ratios of the hydrogen to carbon monoxide in the synthesis gas (synthesis gas or "syngas" is a mixture of gases comprising various ratios of carbon monoxide and hydrogen) can be readily changed by the addition of either hydrogen or carbon monoxide to the syngas stream. In an additional example, the hydrogen:carbon monoxide mole ratio can range from about 3:7 to about 8:2. Typically, the hydrogen:carbon monoxide mole ration will be about 1:1, the mole ratio that matches the stoichiometry of the hydroformylation reaction. Inert gases may also be present in the gas stream, but as this leads to an increase in total pressure, it is generally undesirable.

The reaction conditions are not critical for the operation of the process and conventional hydroformylation conditions normally are used. The process may be carried out at temperatures in the range of about 20° to about 200° C. Additional examples of typical temperature ranges for the operation of our process are from 50° to about 135° C. and about 75° to about 125° C. Higher reactor temperatures are not favored because of increased rates of catalyst decomposition while lower reactor temperatures result in relatively slow reaction rates. The total reaction pressure may range from about 1 bar to about 350 bars absolute (about 5000 psig). In another example, the pressure can range from about 105 to about 175 bars absolute (about 1500 to 2500 psig).

The formaldehyde employed in the process can be utilized in any of its various forms, including, but not limited to, gaseous formaldehyde, aqueous formaldehyde solutions such as, for example, commercially available formalin containing approximately 40% formaldehyde, trioxane or paraformaldehyde, methylene dicarboxylates, and linear polymers of formaldehyde (i.e., poly(oxymethylene) glycols and derivatives thereof) formed from the polymerization or oligomerization of formaldehyde in water, alcohols, or other solvents. Thus, the term "formaldehyde", as used herein in the context of the current specification and claims, is intended to include all the various forms of formaldehyde described above. For example, the formaldehyde can comprise paraformaldehyde, formalin, or a combination thereof. In another embodiment, the process may employ paraformaldehyde as the formaldehyde source.

In some instances, the presence of water in the catalyst solution can reduce the rate of the hydroformylation reaction such that it may be desirable to limit the concentration of water in the catalyst solution. For example, the use of commercial formalin, which contains approximately 60 weight percent water, as a formaldehyde source can severely reduce the rate of the reaction if the concentration of water in the reaction mixture is allowed to become too high. Thus, if water is present in the formaldehyde source, it may be desirable to reduce the overall concentration of water introduced into the reaction by using a feedstock having high concentration of formaldehyde or mixing the aqueous formaldehyde source with a non-aqueous source such as, for example, paraformaldehyde. In one embodiment of the process of the invention, for example, the reaction mixture can have a water concentration of 10 weight percent or less, based on the total weight of the reaction mixture. Other examples of water concentrations in the reaction mixture are 8 weight percent or less, 6 weight percent or less, 4 weight percent or less, 2 weight percent or less, and 0.5 weight percent or less.

The catalyst for the process of the invention comprises rhodium, which may be elemental rhodium, or a rhodium compound, complex or salt, or mixtures thereof, employed as such or deposited or affixed to a solid support such as molecular sieve zeolites, alumina, silica, ion exchange resins or a polymeric ligand. Examples of rhodium compounds that may be used as a source of rhodium for the active catalyst include rhodium(II) or rhodium(II) salts of carboxylic acids, examples of which include di-rhodium tetraacetate dihydrate, rhodium(II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable sources of rhodium. Less desirable rhodium sources are rhodium salts of strong mineral acids such as chlorides, bromides, nitrates, sulfates, phosphates and the like.

In addition to rhodium, the catalyst may further comprise one or more organic ligands as described, for example, in U.S. Pat. No. 3,527,809, or combinations of one or more of these substances. For example, the organic ligand may comprise at least one trivalent organophosphorus compound. In one embodiment, for example, the ligand may comprise at least one tertiary phosphine, tertiary phosphite, fluorophosphite, or combinations thereof. Further examples of trivalent organophosphorus compounds include, but are not limited to, triaryl and tricycloalkyl phosphites and triarylphosphines. Some examples of tertiary phosphines that can be used in the process of the invention include, but are not limited to, trimethylphosphine; ethyl-bis(beta-phenylethyl)phosphine; triethylphosphine; tricyclopentylphosphine; tri-n-butylphosphine; tricyclohexylphosphine; triamylphosphines; dimethylcyclopentylphosphine; trihexylphosphines tri-octylphosphine; tripropylphosphine; dicyclohexyl-methylphosphine; trinonylphosphines; phenyldiethylphosphine; tridecyl-phosphines; dicyclohexylphenylphosphine; triethylhexylphosphine; diphenylmethylphosphine; di-n-butyl octadecylphosphine; diphenyl-butylphosphine; dimethylethylphosphine; diphenylbenzylphosphine; diamylethylphosphine; trilaurylphosphine; and tris(dimethylphenyl)phosphine. In one embodiment, for example, the ligand can comprise triphenyl phosphine.

The organophosphorus-containing catalysts can be prepared by established methods known in the art and described, for example, U.S. Pat. No. 3,527,809. The catalyst can be employed in soluble form or in suspension in the reaction medium, or alternatively deposited on porous supports. The catalyst can be prepared by various techniques. For example, a rhodium complex with carbon monoxide can be preformed and then introduced into the reaction medium or, alternatively, the catalyst can be formed in situ by reaction of rhodium, or rhodium compound, directly with carbon monoxide which may be effected in the presence of the ligand to form one or more organic ligand-carbon monoxide-rhodium complexes in the reaction medium.

In addition to the compounds noted above, we have found that a specific group of phosphorous acid esters, fluorophosphites, can be used as the phosphorus ligand in the hydroformylation of formaldehyde. Thus, the fluorophosphite ligands for the present invention are trivalent phosphorus compounds having the formula (I):

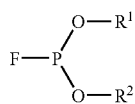

I

The hydrocarbyl groups represented by $R^1$ and $R^2$ may be the same or different, separate or combined, and are selected from unsubstituted and substituted alkyl, cycloalkyl, aralkyl, and aryl groups containing a total of up to about 40 carbon atoms. The total carbon content of substituents $R^1$ and $R^2$ generally is in the range of about 2 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. Typical examples of alkyl, cycloalkyl, and aralkyl groups which $R^1$ and/or $R^2$ individually can represent are alkyl radicals containing up to about 8 carbon atoms, benzyl, cyclopentyl, cyclohexyl, and cycloheptyl.

Examples of the aryl groups which $R^1$ and/or $R^2$ individually can represent include, but are not limited to, carbocyclic aryl groups such as phenyl, naphthyl, anthracenyl, and substituted derivatives thereof. For example, $R^1$ and/or $R^2$ individually can represent aryl radicals having formulas (II-IV):

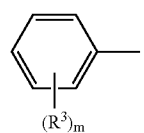

II

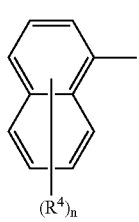

III

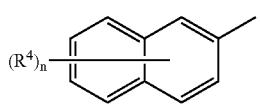

IV wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. Typically, $R^3$ and $R^4$ represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 35 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given hereinbelow as formulas (V), (VI) and (VII).

The divalent groups that $R^1$ and $R^2$ collectively may represent include radicals having the formula

wherein
  each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$;
  X is (i) a chemical bond directly between ring carbon atoms of $A^1$ and $A^2$; or (ii) an oxygen atom, a group having the formula —$(CH_2)_y$— wherein y is 2 to 4, or a group having the formula

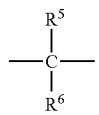

wherein $R^5$ is hydrogen, alkyl or aryl, such as, for example, the aryl groups illustrated by formulas (II), (III) and (IV), and $R^6$ is hydrogen or alkyl. The total carbon content of the group —$C(R^5)(R^6)$- normally will not exceed 20 and, can be in the range of 1 to 8 carbon atoms. Normally, when $R^1$ and $R^2$ collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals having the formulas (V-VII):

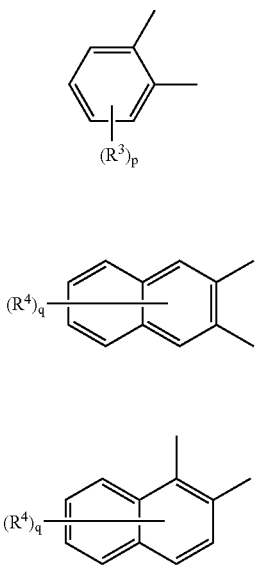

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent lower alkyl groups, i.e., straight-chain and branched-chain alkyl of up to about 4 carbon atoms, and p and q each represent 0, 1 or 2.

In one embodiment, the fluorophosphite esters can be compounds wherein the fluorophosphite ester oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, one or both of the ring carbon atoms that are in a position ortho to the ring carbon atoms bonded to the fluorophosphite ester oxygen atom can be substituted with an alkyl group, especially a branched chain alkyl group such as isopropyl, tert-butyl, tert-octyl and the like. Similarly, when $R^1$ and $R^2$ collectively represent a radical having the formula,

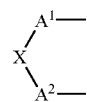

the ring carbon atoms of arylene radicals $A^1$ and $A^2$ that are in a position ortho to the ring carbon atoms bonded to the fluorophosphite ester oxygen atom can be substituted with an alkyl group, typically a branched chain alkyl group such as, for example, isopropyl, tert-butyl, tert-octyl and the like. For example, the fluorophosphite esters may have the general formula (VIII):

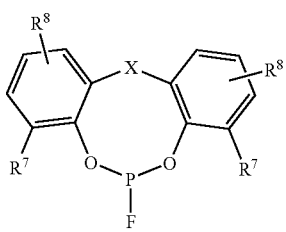

wherein
each $R^7$ is halogen or alkyl of 3 to 8 carbon atoms; each $R^8$ is hydrogen, halogen, alkyl of 1 to 8 carbon atoms, or alkoxy of 1 to 8 carbon atoms; and X is (i) a chemical bond directly between ring carbon atoms of each phenylene group to which X is bonded; or (ii) a group having the formula

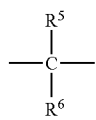

wherein each of $R^5$ and $R^6$ is hydrogen or alkyl of 1 to 8 carbon atoms. In one embodiment, for example, the fluorophosphite can have the following formula (IX):

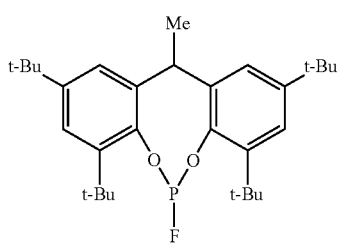

wherein t-Bu is tertiary butyl and Me is methyl. Fluorophosphite (IX) is available commercially from Albemarle Corporation under the trademark ETHANOX 398™ (CAS #118337-09-0).

The fluorophosphite compounds of formula (I) may be prepared by published procedures or by techniques analogous thereto, See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. In addition, some fluorophosphite esters of formula (I) are available commercially such as, for example, fluorophosphite (IX) discussed above.

As noted above, rhodium compounds that may be used as a source of rhodium for catalyst containing fluorophosphite ligands include rhodium(II) or rhodium(III) salts of carboxylic acids, examples of which include di-rhodium tetraacetate dihydrate, rhodium(II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable rhodium feeds. Additionally, in cases where the phosphine moieties of the complex are easily displaced by the fluorophosphite ligands of the present invention, the rhodium component may be introduced into the process as rhodium organophosphine complexes such as, for example, tris(triphenylphosphine) rhodium carbonyl hydride. Less desirable rhodium sources are rhodium salts of strong mineral acids such as chlorides, bromides, nitrates, sulfates, phosphates and the like.

The ratio of gram moles organic ligand to gram atoms rhodium in the hydroformylation catalyst solution and hydroformylation process described herein can vary over a wide range. For example, the gram mole organic ligand:gram atom rhodium ratios may be from about 1:1 to about 200:1. Other examples of gram mole organic ligand:gram atom rhodium ratios are about 1:1 to about 70:1 and about 1:1 to about 50:1.

The concentration of the rhodium and ligand in the hydroformylation solvent or reaction mixture is not critical for the successful operation of our invention. As mentioned hereinabove, a gram mole organic ligand:gram atom rhodium ratio of at least 1:1 normally is maintained in the reaction mixture. The absolute concentration of rhodium in the reaction mixture may vary from about 1 mg/liter to about 5000 mg/liter or more. When the process is operated within the practical conditions of this invention, the concentration of rhodium in the reaction mixture normally is in the range of about 20 to about 300 mg/liter. Concentrations of rhodium lower than this range generally do not yield acceptable reaction rates and/or require reactor operating temperatures that are so high as to be detrimental to catalyst stability. Higher rhodium concentrations are not generally used because of the high cost of rhodium.

The hydroformylation solvent for the process of the invention comprises at least one aprotic amide solvent that exhibits low miscibility with water. For example, the hydroformylation solvent can comprise a tertiary amide containing 14 to 18 carbon atoms. In one embodiment of the invention, the hydroformylation solvent comprises at least one N,N-dihexylbutyramide. For example, the hydroformylation solvent can comprise N,N-di-n-hexyl-n-butyramide, N,N-diisohexyl-n-butyramide, N,N-di-n-hexyl-isobutyramide, N,N-diisohexyl-isobutyramide, or combinations thereof. In another example, the hydroformylation solvent comprises N,N-di-n-hexyl-n-butyramide, N,N-di-n-hexyl-isobutyramide, or combinations thereof. In yet another embodiment of the invention, the hydroformylation solvent comprises N,N-di-n-hexyl-n-butyramide, N,N-di-n-hexyl-isobutyramide, or combinations thereof and the process produces glycolaldehyde at a selectivity from formaldehyde of about 90 to about 100 percent. The term "selectivity", as used herein with respect to glycolaldehyde is the total moles of glycolaldehyde produced divided by the total moles of formaldehyde reacted in the process. Other examples of selectivity to glycolaldehyde from formaldehyde which may be exhibited by the process of the invention are about 92 to about 100 percent, about 95 to about 100 percent, and about 97 to about 100 percent.

The amides described above either commercially available or can be prepared by known reactions. It is understood that any of the above amides may be used in combination with any of the organic ligands described above in any combination and in any ratio with rhodium described herein. For example, the above N,N-di-n-hexyl butyramides described above may be used in any combination with triphenyl phosphine or the fluorophosphite compounds represented by formulas (VIII) or (IX).

Extraction of the hydroformylation reaction mixture with water can be used to separate the glycolaldehyde product from the catalyst and solvent. The process of the invention, therefore, comprises (ii) contacting the hydroformylation reaction mixture with water to produce an organic layer comprising the rhodium catalyst and the hydroformylation solvent, and an aqueous layer comprising glycolaldehyde.

The contacting of the hydroformylaton reaction mixture with water can be carried out by any means which results in intimate or thorough mixing between the aqueous and organic phases. Such means are well-known to persons skilled in the art. Examples of mixing means include, but are not limited to, jet mixers, injectors, agitated tanks and vessels, orifices, mixing nozzles, pumps, agitated line mixers, packed tubes, pipe lines, and mechanical agitation. The mixing can occur in both multi-state countercurrent or cross-flow modes. Typically 1 to 8 stages, more preferably 2 to 6 stages, of cross-flow or countercurrent extraction is sufficient to recover most of the glycolaldehyde produced in the hydroformylation.

The ratio by volume of the reaction mixture to water is controlled to extract most of the glycolaldehyde product without creating an excessively large aqueous layer. For example, the ratio of the volume of the organic layer to the aqueous layer can be about 1:1 to about 5:1. In another example, the volume ratio of organic and aqueous layers can be about 1.2:1 to about 2.5:1.

The contacting step (ii) can be conducted at any temperature from about 20° C. up to about 120° C., although temperatures above 100° C., typically, will require pressurized equipment. In practice, the extraction are generally conducted at a temperature of about 60 to about 90° C. Temperatures lower than 60° C. may lead to slow separation of the phases and, generally, there is little added benefit in operating in excess of 90° C. The contacting step (ii) can be operated at any pressure from atmospheric pressure up to about 175 bar gauge (about 2500 psig). For example, step (ii) may be carried out from atmospheric pressure up to about 2 bar gauge.

The aqueous layer typically comprises about 0.5 to about 20 weight percent glycolaldehyde. Some additional, non-limiting examples of weight percent ranges of glycolaldehyde in the aqueous layer are about 2 to about 15 weight percent and about 3 to about 10 weight percent. The water layer also may contain unreacted formaldehyde in any one of its various forms such as, for example, monomeric formaldehyde, paraformaldehyde, oligomeric formaldehyde, and mixtures thereof. Occasionally, emulsions may occur at the interface of the organic and aqueous phases. When emulsions do occur, they can be readily broken by conventional means such as filtration, heating, or the addition of added solvents. Hydrocarbon cosolvents may be added to the organic phase of the extraction step to facilitate the separation into discrete layers. Examples of hydrocarbon cosolvents include, but are not limited to, aliphatic and aromatic hydrocarbons containing 5 to 20 carbon atoms such as, for example, alkanes, and cycloalkanes such as dodecane, decalin, octane, iso-octane mixtures, cyclohexane, cyclooctane, cyclododecane, methylcyclohexane; aromatic hydrocarbons such as benzene, toluene, xylenes (i.e., ortho, meta, para isomers, individually or mixtures thereof), tetralin, cumene, isomers of diisopropylbenzene, triisopropylbenzene and tert-butylbenzene; and crude hydrocarbon mixtures such as naphtha, mineral oils and kerosene. In one example, the hydrocarbon cosolvents can be chosen from toluene, xylenes, or a mixture thereof.

The process of the invention may further comprise (iii) separating the organic and aqueous layers; and (iv) recycling the organic layer to step (i). The organic layer and aqueous layers may be separated by decantation or other means well known in the art. The organic layer containing the catalyst and hydroformylation solvent may be recycled and reused in the hydroformylation reaction without further purification. To control by-product levels, a small amount of the organic layer can be removed prior to recycling as a purge stream and distilled to recover the hydroformylation solvent and catalyst values. The aqueous layer, comprising the glycolaldehyde may be distilled or evaporated to remove excess water or azeotropically dried. The glycolaldehyde, for example, may be concentrated by distillation or evaporation of any excess water. Optionally, the glycolaldehyde present in the aqueous layer may be hydrogenated to ethylene glycol in the presence of a hydrogenation catalyst such as, for example, Raney nickel, copper chromite, and the like.

Our invention also provides a process for the preparation of glycolaldehyde which comprises: (i) contacting hydrogen, carbon monoxide, and formaldehyde in the presence of a catalyst comprising rhodium and an organic ligand comprising one or more tertiary phosphines, tertiary phosphites, fluorophosphites, or combinations thereof; and a solvent comprising N,N-di-n-hexyl-n-butyramide, N,N-di-n-hexyl-isobutyramide, or a mixture thereof; at a temperature of about 75 to about 135° C. and a pressure of about 105 to about 175 bar absolute, to form a reaction mixture comprising glycolaldehyde; (ii) contacting the reaction mixture with water to produce an organic layer comprising the rhodium catalyst and the hydroformylation solvent, and an aqueous layer comprising the glycolaldehyde; (iii) separating the organic and aqueous layers; and (iv) recycling the organic layer to step (i).

The above embodiment is intended and understood to include the various embodiments of the carbon monoxide, hydrogen, formaldehyde, operating temperatures and pressures, ligands, solvents, extraction and recycling as described hereinabove. For example, the organic ligand can comprise triphenyl phosphine, at least one fluorophosphite compound having formulas (VIII) or (IX), or combinations thereof:

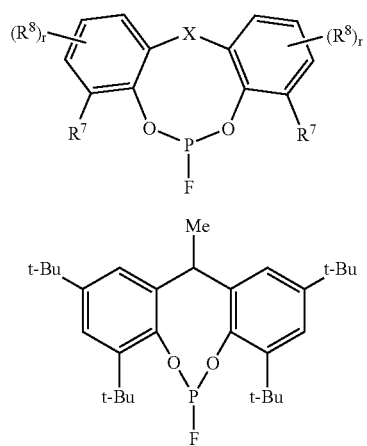

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; t-Bu is tertiary butyl and Me is methyl; and X is a group having the formula

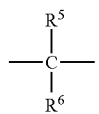

wherein $R^5$ and $R^6$ each are hydrogen or alkyl.

The ratio of gram moles organic ligand to gram atoms rhodium in the hydroformylation process are as described previously. For example, the gram mole organic ligand:gram atom rhodium ratios may be from about 1:1 to about 100:1. Other examples of gram mole organic ligand:gram atom rhodium ratios are about 1:1 to about 70:1 and about 1:1 to about 50:1.

As noted hereinabove, a gram mole organic ligand:gram atom rhodium ratio of at least 1:1 normally is maintained in the reaction mixture. The absolute concentration of rhodium in the reaction mixture or solution may vary from about 1 mg/liter to about 5000 mg/liter or more. When the process is operated within the practical conditions of this invention, the concentration of rhodium in the reaction solution normally is in the range of about 20 to about 300 mg/liter.

The hydroformylation solvent is as described previously. In one embodiment of the invention, for example, the hydroformylation solvent comprises N,N-di-n-hexyl-n-butyramide, N,N-di-n-hexyl-isobutyramide, or combinations thereof and produces glycolaldehyde at a selectivity from formaldehyde of about 90 to about 100 percent. The term "selectivity", as used herein with respect to the glycolaldehyde product, means the total moles of glycolaldehyde produced divided by the total moles of formaldehyde converted to all products. Other examples of selectivity to glycolaldehyde from formaldehyde which may be exhibited by the process of the invention are about 92 to about 100 percent, about 95 to about 100 percent, and about 97 to about 100 percent.

The catalyst solution may comprise other catalyst metals, ligands, solvents, and promoters in addition to the fluorophosphite compounds, rhodium, and hydroformylation solvents described above. For example, Lewis and Bronsted acids such as, for example, $ZnCl_2$ and p-toluenesulfonic acid, can be added to the catalyst solution to enhance the rate or selectivity of the hydroformylation reaction. Other examples of promoters include amine bases such as triethyl amine. These promoters, however, also can have detrimental effects on the catalyst and selectivity of the reaction. For example, the presence of strong acids, such as p-toluenesulfonic acid, can cause the eventual decomposition of fluorophosphite ligands. Similarly, amines can catalyze the aldol condensation of the product glycolaldehyde with itself to form heavy byproducts.

Any of the known hydroformylation reactor designs or configurations may be used in carrying out the process provided by the present invention. For example, the process also may be practiced in a batchwise manner by contacting the formaldehyde, hydrogen and carbon monoxide with the catalyst in an autoclave. In another example, a reactor design where catalyst and feedstock are pumped into a reactor and allowed to overflow with product glycolaldehyde, i.e. liquid overflow reactor design, is also suitable. For example, glycolaldehyde product may be prepared in a continuous manner with the glycolaldehyde product being removed from the reactor zone as a liquid in combination with the catalyst. The glycolaldehyde product may be separated from the catalyst by as described above and the organic layer containing the catalyst and solvent recycled back to the reactor. A trickle-bed reactor design also is suitable for this process. It will be apparent to those skilled in the art that other reactor schemes may be used with this invention. The various embodiments of the present invention are further illustrated by the following examples.

EXAMPLES

General—All hydroformylation reaction product analyses were conducted by gas chromatography. The water insoluble organic samples were analyzed by use of an internal standard method using n-butyl benzoate as an internal standard. The samples were analyzed on a 30 meter by 320 micron RTX-200 column with a 0.25 micron film. The initial temperature of the oven was 40° C. (4 minute hold) and then the temperature was programmed at 12° C. per minute to a final temperature of 29° C. (30 minute hold). Water extract phases were analyzed in a similar manner except that dimethylacetamide was used as the internal standard. The conversion of formaldehyde was calculated as the moles of formaldehyde reacted divided by the total moles of formaldehyde (as paraformaldehyde) present at the start of the reaction. Selectivities to various products were calculated as the total moles of product divided by the moles of formaldehyde reacted.

Examples 1-3 and Comparative Examples 1-22

A 300 ml Autoclave Engineer™ autoclave was charged with 0.25 Mole of paraformaldehyde, the amide solvent and mixed xylenes (i.e., a mixture of ortho, meta, and para xylenes) as specified in Table 1, 1.57 grams of triphenylphosphine and 0.075 grams of rhodium (I) dicarbonyl acetonylacetonate. The reactor was purged with $N_2$ and charged with a 1:1 molar mixture of hydrogen and carbon monoxide to a total pressure of 138 bar gauge (2000 psig). The reactor was stirred and heated to a temperature of 100° C. to 110° C. for a total time of 1 hour. The reaction pressure was allowed to increase on heat up and drop as the reaction progressed. If the gas consumption was sufficient to drop the reactor pressure to 138 bar gauge (2000 psig), then the pressure was maintained at 138 bar gauge (2000 psig) with additional syn gas. Upon completion of the run, the reactor was cooled and the excess pressure vented. The contents of the autoclave were examined by gas chromatography using an internal standard GC method. The results are presented in Table 1.

TABLE 1

Comparison of Amide Solvents for the Hydroformylation of Formaldehyde

| Exp | Amide Solvent | Amide Solvent (grams) | Mixed Xylenes (mL) | % Conv. of $H_2CO$ | % Select. to GA | % Select. to Methanol |
|---|---|---|---|---|---|---|
| 1 | 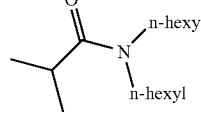 | 40 | 10 | 41.6 | 92.7 | 1.3 |
| 2 | 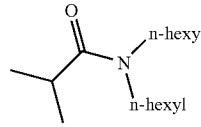 | 40 | 10 | 43.9 | 93.8 | 1.1 |
| 3 | 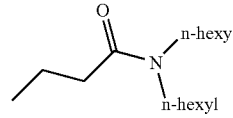 | 40 | 10 | 40.8 | 99.0 | 1.0 |
| C1 | 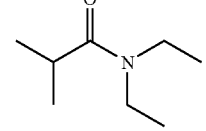 | 40 | 10 | 0.0 | 0.0 | 0.0 |
| C2 | 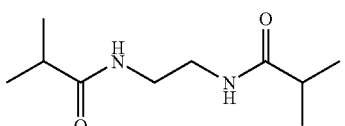 | 40 | 10 | 0.0 | 0.0 | 0.0 |
| C3 | 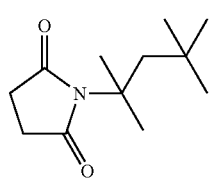 | 30 | 20 | 0.0 | 0.0 | 0.0 |

TABLE 1-continued

Comparison of Amide Solvents for the Hydroformylation of Formaldehyde

| Exp | Amide Solvent | Amide Solvent (grams) | Mixed Xylenes (mL) | % Conv. of $H_2CO$ | % Select. to GA | % Select. to Methanol |
|---|---|---|---|---|---|---|
| C4 | N-cyclohexyl succinimide | 30 | 20 | 5.0 | 61.7 | 0.0 |
| C5 | N-n-octyl phthalimide | 30 | 20 | 6.7 | 59.9 | 3.1 |
| C6 | N,N,N',N'-tetra(n-hexyl) isophthalamide | 30 | 20 | 10.1 | 100.0 | 0.0 |
| C7 | N-(2,2,4-trimethylpentyl) isobutyramide | 40 | 20 | 11.8 | 72.7 | 0.0 |
| C8 | 1-butyryl morpholine | 40 | 20 | 13.7 | 95.0 | 5.0 |
| C9 | N,N-diisopropyl isobutyramide | 40 | 10 | 13.9 | 73.4 | 0.0 |
| C10 | N,N'-bis(isobutyryl)-2-methyl-1,4-butanediamine | 30 | 20 | 17.9 | 99.6 | 0.0 |
| C11 | N,N-di(n-hexyl) benzamide | 40 | 10 | 18.3 | 35.5 | 0.0 |
| C12 | N-(2-ethylhexyl) isobutyramide | 40 | 10 | 18.6 | 70.6 | 0.0 |

TABLE 1-continued

Comparison of Amide Solvents for the Hydroformylation of Formaldehyde

| Exp | Amide Solvent | Amide Solvent (grams) | Mixed Xylenes (mL) | % Conv. of $H_2CO$ | % Select. to GA | % Select. to Methanol |
|---|---|---|---|---|---|---|
| C13 | iBu-C(O)-NH-CH2-CH(CH3)-CH2-NH-C(O)-iBu | 30 | 20 | 20.8 | 88.8 | 0.0 |
| C14 | (n-hexyl)2N-C(O)-CH2-CH2-C(O)-N(n-hexyl)2 | 40 | 10 | 22.2 | 20.9 | 0.0 |
| C15 | iBu-C(O)-NH-n-octyl | 40 | 10 | 23.9 | 88.6 | 0.0 |
| C16 | iBu-C(O)-morpholine | 40 | 10 | 25.0 | 66.4 | 2.9 |
| C17 | n-Pr-C(O)-NH-CH2-C(CH3)2-CH2-C(CH3)3 | 30 | 10 | 26.3 | 33.8 | 0.0 |
| C18 | (n-hexyl)2N-C(O)-(CH2)3-C(O)-N(n-hexyl)2 | 40 | 10 | 26.7 | 36.7 | 0.0 |
| C19 | (n-hexyl)2N-C(O)-CH2-O-CH2-CH2-O-n-Pr | 40 | 10 | 27.5 | 74.2 | 1.3 |
| C20 | n-Pr-C(O)-NH-cyclohexyl | 40 | 10 | 30.6 | 99.0 | 0.2 |
| C21 | iPr-C(O)-NH-cyclohexyl | 40 | 10 | 32.8 | 29.6 | 57.0 |
| C22 | n-Pr-C(O)-N(iPr)2 | 40 | 10 | 48.7 | 34.0 | 0.7 |

Example 4

Hydroformylation of Formaldehyde and Extraction Utilizing N,N-di-n-hexyl-n-butyramide To 300 milliliter Autoclave Engineer™ stirred autoclave was charged paraformaldehyde (0.25 Mole), mixed xylenes (10 ml), N,N-di-n-hexyl-n-butyramide (40 grams), triphenylphosphine (0.006 Mole), and 0.075 grams of rhodium(I) dicarbonyl acetonylacetonate. The autoclave was sealed, $N_2$ purged, and then pressurized to 138 bar gauge (2000 psig) with a 1:1 mixture of hydrogen and carbon monoxide. The reaction was heated to 100° C. and held under 138 bar gauge (2000 psig) of synthesis gas for one hour. The reaction was then cooled to ambient temperature and the excess gas vented off.

The reaction contents (63 milliliters) were then combined with 50 milliliters of deionized water and mixed thoroughly. The mixture was heated to 75-85° C. to facilitate the separation of the layers. The separation gave two phases, an organic phase of 57 milliliters, an aqueous phase of 53 milliliters and about 3 milliliters of emulsion which was saved and re-charged at the second extraction step below. The aqueous phase was analyzed for rhodium, glycolaldehyde, and N,N-di-n-hexyl n-butyramide. The organic phase was re-charged to the autoclave. The result of the analysis is as shown below. The conversion of formaldehyde to products was 33.9% and the selectivity of converted formaldehyde to glycolaldehyde was 96% as measured by gas chromatography.

TABLE 2

Analysis of Aqueous Extract

| | |
| --- | --- |
| Volume | 53 milliliters |
| Rhodium Content | 0.1 milligrams per liter (0.0053 milligrams total) |
| Glycolaldehyde content | 3.46 grams |
| N,N-di-n-hexyl n-butyramide | Not detectable by GC |
| Formaldehyde | 5.16 grams |

Example 5

Recycling of Organic Layer

The rhodium containing organic phase from the previous extraction (53 milliliters) was re-charged to the autoclave along with 0.25 mole of paraformaldehyde. The autoclave was sealed, purged and allowed to react under the same conditions as the previous run. The autoclave contents were removed from the autoclave and combined with the emulsion layer from the first step and then extracted with 50 milliliters of water. The phases separated at 75-85° C. The phases were analyzed by gas chromatography as described previously. The conversion and selectivity of formaldehyde to glycolaldehyde was about 35 and 98 percent, respectively. The aqueous phase showed only a trace of the butyramide solvent that was below the integration threshold of the gas chromatograph and estimated to be less than 0.1 weight percent of the total amount of butyramide solvent. The amount of amide retained in the organic phase, therefore, was estimated to be greater than 99.9 weight percent. The results of the experiment are shown in Table 3.

TABLE 3

Results of Second Extraction

| | Organic Phase | Aqueous Phase |
| --- | --- | --- |
| Volume | 51 milliliters | 53 milliliters |
| Rhodium Content | 437 ppm (99.976% recovery) | 0.1 ppm (0.024%) |
| Glycolaldehyde content | 0.62 grams | 5.52 grams |
| N,N-di-n-hexyl n-butyramide | >99.9 wt % | trace (<0.1 wt %) |
| Formaldehyde | Not measured | 5.38 grams |

We claim:

1. A process for the preparation of glycolaldehyde, comprising: (i) contacting hydrogen, carbon monoxide, and formaldehyde in the presence of a catalyst comprising rhodium and a solvent comprising at least one N,N-dihexylbutyramide to form a reaction mixture comprising glycolaldehyde; and (ii) contacting said reaction mixture with water to produce an organic layer comprising said rhodium catalyst and said hydroformylation solvent, and an aqueous layer comprising said glycolaldehyde.

2. The process according to claim 1 wherein the concentration of rhodium in said reaction mixture is about 20 to about 1000 mg per liter and said process is carried out at a temperature of about 50 to about 125° C. at a pressure of about 105 to about 175 bar absolute.

3. The process according to claim 1 wherein said hydrogen and carbon monoxide have a total partial pressure of about 0.5 to about 350 bar absolute.

4. The process according to claim 1 wherein the mole ratio of hydrogen to carbon monoxide is about 10:1 to about 1:10.

5. The process according to claim 1 wherein said formaldehyde comprises paraformaldehyde, formalin, or a combination thereof.

6. The process according to claim 5 wherein said formaldehyde comprises paraformaldehyde.

7. The process according to claim 1 wherein said catalyst further comprises an organic ligand comprising at least one trivalent organophosphorus compound at a ratio of gram moles organic ligand to gram atoms rhodium of about 1:1 to about 200:1.

8. The process according to claim 7 wherein said ligand comprises at least one tertiary phosphine, tertiary phosphite, fluorophosphite, or combinations thereof.

9. The process according to claim 8 wherein said organic ligand comprises triphenyl phosphine.

10. The process according to claim 8 wherein said fluorophosphite comprises (i) at least one fluorophosphite compound having the general formula (I):

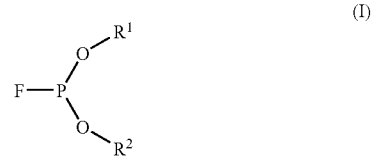

wherein $R^1$ and $R^2$ collectively represent alkylene of 2 to 12 carbon atoms, cyclohexylene, an arylene group having the formula

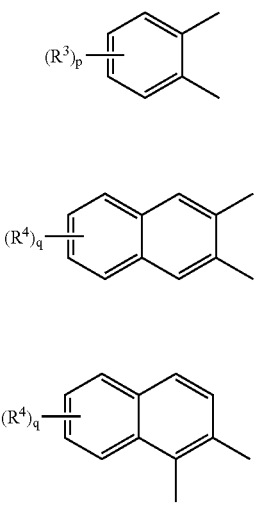

or a radical having the formula

wherein
each of $A^1$ and $A^2$ is an arylene radical having formula (V), (VI) or (VII) above wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula —$(CH_2)_y$— wherein y is 2 to 4, or a group having the formula

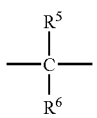

wherein
$R^5$ is hydrogen, alkyl or aryl; $R^6$ is hydrogen or alkyl; and the group —$C(R^5)(R^6)$— contains up to 8 carbon atoms; and wherein
$R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; and p and q each is 0, 1 or 2.

11. The process according to claim 10 wherein said fluorophosphite compound has formula (VIII):

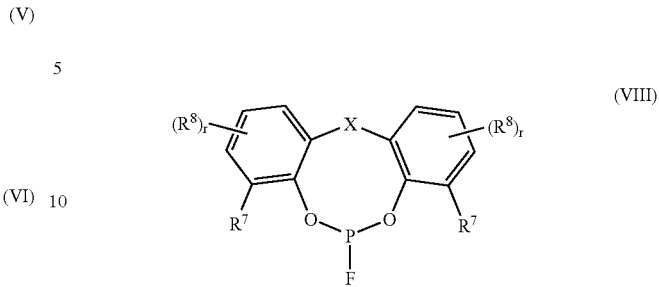

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; and X is a group having the formula

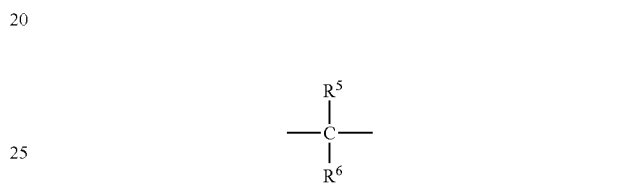

wherein $R^5$ and $R^6$ each are hydrogen or alkyl.

12. The process according to claim 11 wherein said fluorophosphite compound has formula (IX):

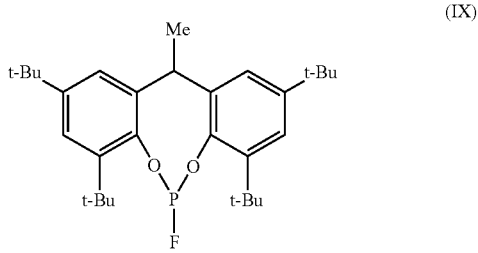

wherein t-Bu is tertiary butyl and Me is methyl.

13. The process according to claim 1 wherein said solvent comprises N,N-di-n-hexyl-n-butyramide, N,N-diisohexyl-n-butyramide, N,N-di-n-hexyl-isobutyramide, N,N-diisohexyl-isobutyramide, or combinations thereof.

14. The process according to claim 13 wherein solvent comprises N,N-di-n-hexyl-n-butyramide, N,N-di-n-hexyl-isobutyramide, or combinations thereof.

15. The process according to claim 1 wherein the solvent further comprises a hydrocarbon cosolvent chosen from benzene, toluene, xylenes, and mixtures thereof.

16. The process according to claim 1 wherein the ratio of said organic layer to said aqueous layer on a volume basis is about 1:1 to about 5:1, and step (ii) is carried out at a temperature of about 20 to about 120° C. and at a pressure of about 1 to about 175 bar absolute.

17. The process according to claim 1 further comprising (iii) separating said organic and aqueous layers; and (iv) recycling said organic layer to step (i).

18. A process for the preparation of glycolaldehyde, comprising: (i) contacting hydrogen, carbon monoxide, and formaldehyde in the presence of a catalyst comprising rhodium and an organic ligand comprising one or more tertiary phosphines, tertiary phosphites, fluorophosphites, or combinations thereof; and a solvent comprising N,N-di-n-hexyl-n-butyramide, N,N-di-n-hexyl-isobutyramide, or a mixture thereof; at a temperature of about 75 to about 135° C. and a pressure of about 105 to about 175 bar absolute, to form a reaction mixture comprising glycolaldehyde; (ii) contacting said reaction mixture with water to produce an organic layer comprising said rhodium catalyst and said hydroformylation solvent, and an aqueous layer comprising said glycolaldehyde; (iii) separating said organic and aqueous layers; and (iv) recycling said organic layer to step (i).

19. The process according to claim 18 wherein said organophosphorus compound comprises triphenyl phosphine, at least one fluorophosphite compound having formulas (VIII) or (IX), or a combination thereof:

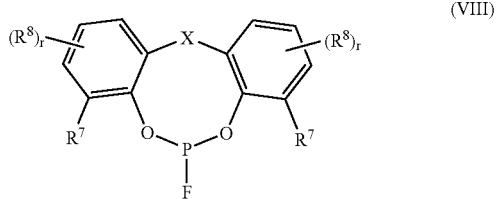
(VIII)

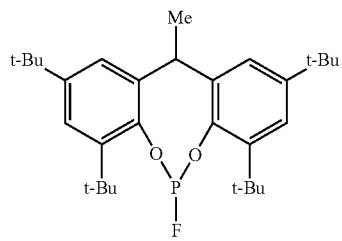
(IX)

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; t-Bu is tertiary butyl and Me is methyl; and X is a group having the formula

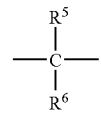

wherein $R^5$ and $R^6$ each are hydrogen or alkyl.

20. The process according to claim 19 wherein said catalyst further comprises a phosphorus ligand at a ratio of gram moles phosphorus ligand to gram atoms rhodium of about 1:1 to about 50:1.

* * * * *